US010729801B2

United States Patent
Woodbridge

(10) Patent No.: US 10,729,801 B2
(45) Date of Patent: Aug. 4, 2020

(54) METHOD AND SYSTEM FOR GENERATING NON-THERMAL PLASMA

(71) Applicant: Terrance Woodbridge, Cary, NC (US)

(72) Inventor: Terrance Woodbridge, Cary, NC (US)

(73) Assignee: PhoenixAIRE, LLC, McLean, VA (US)

( * ) Notice: Subject to any disclaimer, the term of this patent is extended or adjusted under 35 U.S.C. 154(b) by 89 days.

(21) Appl. No.: 16/173,657

(22) Filed: Oct. 29, 2018

(65) Prior Publication Data
US 2019/0125920 A1    May 2, 2019

Related U.S. Application Data

(63) Continuation of application No. 14/922,975, filed on Oct. 26, 2015, now Pat. No. 10,111,977.

(60) Provisional application No. 62/187,410, filed on Jul. 1, 2015.

(51) Int. Cl.
*A61L 9/22* (2006.01)
*H05H 1/48* (2006.01)

(52) U.S. Cl.
CPC .............. *A61L 9/22* (2013.01); *H05H 1/48* (2013.01); *A61L 2209/111* (2013.01); *A61L 2209/14* (2013.01); *A61L 2209/212* (2013.01); *H05H 2001/483* (2013.01); *H05H 2245/1225* (2013.01)

(58) Field of Classification Search
CPC ....... A61L 9/22; H05H 1/48; H05H 2001/483
See application file for complete search history.

(56) References Cited

U.S. PATENT DOCUMENTS

| | | | |
|---|---|---|---|
| 906,468 | A | 12/1908 | Steynis |
| 1,157,859 | A | 10/1915 | Freet |
| 1,454,219 | A | 5/1923 | Goedicke |
| 1,505,669 | A | 8/1924 | Quain |

(Continued)

FOREIGN PATENT DOCUMENTS

| CN | 1312448 | 4/2007 |
|---|---|---|
| DE | 1923081 | 11/1970 |

(Continued)

OTHER PUBLICATIONS

Marsden, James L., Evaluation of AirOcare Reaction Chamber and Reactive Oxygen Species for Reducing Methicillin Resistant *Staphylococcus aureus*, Acinetobacter Baumannii and Listeria Monocytogenes on Stainless Steel, Plastic and Polyethylene Surfaces (Executive Summary), K-State Food Science Institute, Kansas State University, Manhattan, KS 66506, Retrieved Feb. 19, 2016.

(Continued)

*Primary Examiner* — Kevin Joyner
(74) *Attorney, Agent, or Firm* — Wiley Rein LLP

(57) ABSTRACT

Disclosed herein are apparatuses and methods for generating non-thermal plasma which can form reactive oxygen species (ROS), such as those used to neutralize bacteria and other pathogens in the air and surrounding area. Also disclosed are apparatuses and methods for neutralizing bacteria and other pathogens using ROS generated through the use of non-thermal plasma. Also disclosed are apparatuses and methods for generating ROS. Also disclosed are apparatuses and methods for treating air and nearby surfaces.

15 Claims, 5 Drawing Sheets

(56) References Cited

U.S. PATENT DOCUMENTS

| | | | |
|---|---|---|---|
| 2,162,809 A | 6/1939 | Groak et al. |
| 2,687,781 A | 8/1954 | Sens |
| 2,778,443 A | 1/1957 | Yereance |
| 3,730,874 A | 5/1973 | Trub |
| 3,833,492 A | 9/1974 | Bollyky |
| 3,921,002 A | 11/1975 | Williams et al. |
| 3,967,131 A | 6/1976 | Slipiec |
| 4,025,441 A | 5/1977 | Tabata et al. |
| 4,048,668 A | 9/1977 | Von Bargen et al. |
| 4,049,552 A | 9/1977 | Arif |
| 4,051,045 A | 9/1977 | Yamamoto et al. |
| 4,079,260 A | 3/1978 | Dmitriev et al. |
| 4,101,783 A | 7/1978 | Hutter |
| 4,123,664 A | 10/1978 | Yamamura et al. |
| 4,128,768 A | 12/1978 | Yamamoto et al. |
| 4,159,971 A | 7/1979 | Gneupel |
| 4,216,096 A | 8/1980 | Pare et al. |
| 4,234,800 A | 11/1980 | Kenly et al. |
| 4,323,379 A | 4/1982 | Shearin |
| 4,383,976 A | 5/1983 | Notaro |
| 4,411,756 A | 10/1983 | Bennett et al. |
| 4,417,966 A | 11/1983 | Krauss et al. |
| 4,461,744 A | 7/1984 | Emi et al. |
| 4,504,446 A | 3/1985 | Kunicki et al. |
| 4,614,573 A | 9/1986 | Masuda |
| 4,640,782 A | 2/1987 | Burleson |
| 4,650,573 A | 3/1987 | Nathanson |
| 4,656,010 A | 4/1987 | Leitzke et al. |
| 4,690,803 A | 9/1987 | Hirth |
| 4,696,800 A | 9/1987 | Sasaki et al. |
| 4,725,412 A | 2/1988 | Ito |
| 4,764,349 A | 8/1988 | Arff et al. |
| 4,877,588 A | 10/1989 | Ditzler et al. |
| 4,878,642 A | 11/1989 | Kirby, Jr. |
| 4,886,645 A | 12/1989 | Fischer et al. |
| 4,960,569 A | 10/1990 | Fovell et al. |
| 4,981,656 A | 1/1991 | Leitzke |
| 5,004,587 A | 4/1991 | Tacchi |
| 5,008,087 A | 4/1991 | Batchelor |
| 5,015,442 A | 5/1991 | Hirai |
| 5,034,198 A | 7/1991 | Kaiga et al. |
| 5,093,087 A | 3/1992 | Freeman |
| 5,124,132 A | 6/1992 | Francis, Jr. et al. |
| 5,145,653 A | 9/1992 | Fischer et al. |
| 5,268,151 A | 12/1993 | Reed et al. |
| 5,387,842 A | 2/1995 | Roth et al. |
| 5,411,713 A | 5/1995 | Iwanaga |
| 5,508,008 A | 4/1996 | Wasser |
| 5,523,057 A | 6/1996 | Mazzilli |
| 5,833,740 A | 11/1998 | Brais |
| 5,961,920 A | 10/1999 | Söremark |
| 5,989,303 A | 11/1999 | Hodge |
| 5,997,428 A | 12/1999 | Kagata et al. |
| 6,039,214 A | 3/2000 | Hewett |
| 6,066,348 A | 5/2000 | Yuan et al. |
| 6,165,423 A | 12/2000 | Crosbie |
| 6,228,149 B1 | 5/2001 | Alenichev et al. |
| 6,280,691 B1 | 8/2001 | Homeyer et al. |
| 6,358,478 B1 | 3/2002 | Söremark |
| 6,481,219 B2 | 11/2002 | Palermo |
| 6,503,547 B1 | 1/2003 | Lima |
| 6,528,023 B2 | 3/2003 | Fleischer |
| 6,613,277 B1 | 9/2003 | Monagan |
| 6,620,385 B2 | 9/2003 | Fujii |
| 6,630,105 B1 | 10/2003 | O'Neill et al. |
| 6,811,757 B2 | 11/2004 | Niv et al. |
| 6,866,828 B2 | 3/2005 | Segawa et al. |
| 6,893,610 B1 | 5/2005 | Barnes |
| 6,991,768 B2 | 1/2006 | Keras et al. |
| 7,651,555 B2 | 1/2010 | Roseberry et al. |
| 2003/0066285 A1 | 4/2003 | Raybone et al. |
| 2003/0072675 A1 | 4/2003 | Takeda et al. |
| 2003/0121770 A1 | 7/2003 | McNulty, Jr. |
| 2004/0135379 A1 | 7/2004 | Meier et al. |
| 2004/0175318 A1 | 9/2004 | Segawa et al. |
| 2004/0184972 A1 | 9/2004 | Kelly et al. |
| 2004/0262241 A1 | 12/2004 | Socha |
| 2005/0023128 A1 | 2/2005 | Keras et al. |
| 2005/0169821 A1 | 8/2005 | Boschert et al. |
| 2005/0186108 A1 | 8/2005 | Fields |
| 2006/0233660 A1 | 10/2006 | Furuhashi et al. |
| 2007/0041882 A1 | 2/2007 | Roseberry et al. |
| 2008/0035472 A1* | 2/2008 | Lepage ............ A61L 9/16 204/229.8 |
| 2008/0199351 A1 | 8/2008 | Woodbridge |
| 2010/0254868 A1 | 10/2010 | Obee et al. |
| 2011/0030320 A1 | 2/2011 | Blumenstock et al. |
| 2011/0280764 A1 | 11/2011 | Benson et al. |
| 2012/0063959 A1 | 3/2012 | Woodbridge et al. |
| 2014/0373817 A1 | 12/2014 | Waddell et al. |

FOREIGN PATENT DOCUMENTS

| | | |
|---|---|---|
| EP | 0560690 | 9/1993 |
| EP | 1125588 | 8/2001 |
| EP | 1508289 | 2/2005 |
| EP | 1968653 | 2/2013 |
| JP | 10511572 | 11/1998 |
| JP | 10314289 | 12/1998 |
| JP | 2001221565 | 8/2001 |
| JP | 2005095649 | 4/2005 |
| WO | 96/20017 | 7/1996 |
| WO | 00/78670 | 12/2000 |
| WO | 03/038351 | 5/2003 |
| WO | 03/092752 | 11/2003 |
| WO | 03/101498 | 12/2003 |
| WO | 04/062800 | 7/2004 |
| WO | 2007064368 | 6/2007 |

OTHER PUBLICATIONS

Falkenberg, R., AirOcare Technology, Creating a Safe Food Environment by Eliminating Influenza A, MRSA, Norovirus, and Rhinovirus on Various Inoculated Surfaces, FSPT, 6 pgs, Retrieved Feb. 19, 2016.

International Preliminary Report on Patentability for PCT/US06/28734 dated Feb. 8, 2012.

Office action for U.S. Appl. No. 11/289,363 dated Jun. 22, 2010.

European Search Opinion dated Oct. 4, 2010.

Supplemental European Search Report, dated Oct. 4, 2010.

Office action for U.S. Appl. No. 11/289,363, dated Jun. 17, 2009.

Fantech: FR Series Fans—Specifications, Retrieved Jun. 14, 2005 from http://www.fantech.net/fr2.htm.

English abstract of JP Publication No. 2005095649, dated Apr. 13, 2012.

English translation of JP Publication No. 10-314289, dated Mar. 23, 2012.

English abstract of CN Publication No. 1312448, dated Aug. 26, 2011.

English abstract of EP Publication No. 1125588, dated Apr. 1, 2011.

English abstract of EP Publication No. 1508289, dated Feb. 20, 2007.

\* cited by examiner

METHOD AND SYSTEM FOR GENERATING NON-THERMAL PLASMA

CROSS-REFERENCE TO RELATED APPLICATIONS

This application is a continuation of U.S. application Ser. No. 14/922,975, filed 26 Oct. 2015, now pending, which claims the benefit of U.S. provisional application No. 62/187,410, filed 1 Jul. 2015, which applications are hereby incorporated by reference as though fully set forth herein.

FIELD OF THE INVENTION

The present invention relates to apparatuses and methods for generating non-thermal plasma which can form reactive oxygen species, which in turn, can be used to neutralize bacteria and other pathogens in the air and surrounding area. The present invention also relates to an apparatuses and methods for neutralizing bacteria and other pathogens using reactive oxygen species generated through the use of non-thermal plasma.

BACKGROUND OF THE INVENTION

Today's high-efficiency particulate arrestance (HEPA) filters do not have the capability to deal with all aspects of indoor air pollution. Although HEPA filters may be effective at filtering out as much as 99.97% of air borne particles that have a size of 0.3 µm or larger, they are not always effective at treating or removing airborne contaminants made up of microorganisms, viruses, and bacteria smaller than 0.3 µm, all of which are potentially harmful. The inventions disclosed herein, through new devices for and new methods of producing Reactive Oxygen Species ("ROS"), have the ability to treat and remove airborne contaminants using processes that produce a non-thermal plasma field from ambient air within a reaction chamber.

One of ordinary skill in the art would understand "non-thermal plasma" to refer to plasma that is not in thermodynamic equilibrium. In particular, as used herein, "non-thermal plasma" refers to plasma that is produced by a process that does not involve the use or generation of substantial heat; in other words, the temperature of the fluid used to generate the plasma (e.g., ambient air) is not substantially increased during the process of generating plasma. It is known in the art that non-thermal plasma contains reactive forms of oxygen, i.e., ROS, that have a much higher reactivity than oxygen in the form of stable oxygen molecules, which include atomic oxygen, singlet oxygen, hydrogen peroxide, superoxide anion, tri-atomic oxygen and hydroxyl radicals. It is known that ROS can react with particles as small as and smaller than about 0.3 microns. The antimicrobial properties of ROS in the air and on surfaces is known, and the mechanisms by which ROS inactivate bacteria has been studied. See, e.g., Suresh G. Joshi, M. Cooper, A. Yost, M. Paff, U. K. Ercan, G. Fridman, G. Friedman, A. Fridman, and A. D. Brooks, "Nonthermal dielectric-barrier discharge plasma-induced inactivation involves oxidative DNA damage and membrane lipid peroxidation in *Escherichia coli*," Antimicrobial Agents Chemotherapy, vol. 55, no. 3, pp. 1053-1062, March 2011 (which article is incorporated by reference in its entirety into this application). It is understood, for example, that the different ROS attach themselves to the surfaces of contaminants and other pathogens at bond sites to create strong oxidizing radicals. These radicals draw out the hydrogen that is present in these contaminants and other pathogens, breaking down the surface membranes and rendering them inactive (in other words, neutralizing the contaminants and pathogens). The end result may be that the hydroxide and hydrogen radicals combine and form water, and the contaminants and pathogens are inactivated and neutralized. Viruses, however, are bundles of nucleic acid surrounded by a protein bases capsid. When viruses are exposed to ROS both the capsid and viral RNA can be destroyed.

Furthermore, the ROS generated in the non-thermal plasma fields described herein can also breakdown Volatile Organic Compounds (VOC). When carbon based VOCs (alcohols, aldehydes, and ketones) pass through the non-thermal plasma, the covalent bonds in the molecules can be broken, which can also produce carbon dioxide and/or oxygen.

Unlike many other low energy technologies, the present invention avoids producing toxic intermediates. The inventions disclosed herein can be used for food preservation, in medical applications, and other industries in which airborne contaminants can be problematic.

BRIEF SUMMARY OF THE INVENTION

One aspect of the inventions disclosed is to provide a system and method for utilizing ambient air to generate ROS to neutralize pathogens, viruses and volatile organic compounds from the air for the purpose of treating the air and the surrounding areas.

Disclosed herein is an air treatment apparatus having an intake portion, an output portion, and a reaction chamber located between the intake portion and output portion. The reaction chamber includes an anode rail assembly and a cathode rail. The anode rail assembly has an anode rail made of a first conductive material and having a longitudinal axis, and a plurality of discharge anode elements. Each of the plurality of discharge anode elements has a proximal end and a distal end, such that the proximal ends of the discharge anode elements are fixed to the anode rail, and each of the plurality of discharge anode elements is electrically coupled to each other and to the anode rail. The cathode rail is made of a second conductive material, and is positioned such that it is substantially parallel to the anode rail, such that the cathode rail is opposite the plurality of discharge anode elements. The anode rail assembly and the cathode rail are located relative to each other so as to form a space, wherein the space has a central longitudinal axis and further wherein the space separates the cathode rail from the plurality of discharge anode elements such that the discharge anode elements do not cross the central longitudinal axis of the space. The air treatment apparatus may also include an intake blower located in the intake portion, wherein the intake blower is configured to draw air into the reaction chamber. The air treatment apparatus also includes power supply circuitry capable of delivering sufficient energy to generate a non-thermal plasma field in the space between the anode rail assembly and the cathode rail. The air treatment apparatus may optionally include a sensor configured to monitor tri-atomic oxygen, and preferably, the sensor may be located externally to the apparatus. In one embodiment the air treatment apparatus may utilize the same material for the first conductive material and the second conductive material, though in another embodiment, the first conductive material may be different from the second conductive material. For example, the first conductive material and second conductive material may each be selected from the group consisting of silver, copper, gold, aluminum, zinc, brass, steel and alloys of the foregoing elements. Optionally, at least a portion of an outer surface of the distal ends of the discharge anode elements may be textured to facilitate formation of plasma, including for example, one or more of grooves, etchings, ridges, dimplings, and pittings. The air treatment apparatus may have a cathode rail which has an upper surface, at least a portion of which surface is textured, such that the textured surface faces the distal ends of the discharge anode elements. The textured surface of the cathode rail may include, for example, comprises one or more of grooves, etchings, ridges, dimplings, and pittings. In addition, the air treatment may include one or more filters, either on the air intake portion or the air output portion.

Also disclosed is an ambient air treatment device, comprising: a reaction chamber having an anode assembly and a cathode rail spaced opposite the anode assembly, an airflow input on a first side of the anode assembly and the cathode rail, and an airflow output on a second side of the anode assembly and the cathode rail; and a power supply coupled to the anode assembly and to the cathode rail capable of generating a plasma field between the anode assembly and the cathode rail. The anode assembly may include a common electrical bus and a plurality of discharge anode elements extending outward from the common electrical bus, said discharge anode elements having a textured surface on a distal end for discharging electrical current. The cathode rail may include one or more conductive elements placed in electrical contact with each other so as to form an electrically-conductive, elongated cathode having an upper face, wherein at least a portion of the upper face contains a textured surface for receiving electrical current. The ambient air treatment device can operate using different power supplies in order to create different volumes of ROS. For example, the ambient air treatment device can operate using a power supply outputting greater than about 1,000 VAC at a frequency of about 60 Hz. Alternatively, the ambient air treatment device can operate using a power supply outputting greater than about 1,000 VAC at a frequency of greater than about 1,000 Hz. Alternatively, the ambient air treatment device can operate using a power supply outputting greater than about 2,000 VAC at a frequency of greater than about 10,000 Hz. Each of the anode assembly and the cathode rail may be made using a conductive material comprising at least one of silver, copper, gold, aluminum, zinc, brass, and steel. For example, the anode assembly may be made using a first conductive material selected from: silver, copper, gold, aluminum, zinc, brass, steel, and stainless steel, and the cathode rail is made using a second conductive material, different from the first conductive material, selected from: silver, copper, gold, aluminum, zinc, brass, steel, and stainless steel. The ambient air treatment device can include an elongated anode assembly having a distance of D, and a cathode rail that is elongated, is substantially flat and has a distance of less than D, wherein the plurality of discharge anode elements extend towards the cathode rail but remain spaced from the cathode rail to permit the creation of a plasma field. The textured surface on the distal end of each of the plurality of discharge anodes, as well as the textured surface on the upper surface of the cathode rail, may each be formed using a variety of formations to facilitate formation of plasma, including for example, one or more of: a cross-hatch pattern, grooves, etchings, ridges, dimplings, and pittings. The ambient air treatment device may optionally include a blower to generate an air flow across the plasma field during operation of the ambient air treatment device.

A method of generating a non-drifting plasma field is also disclosed. The method may include the steps of: drawing air into a reaction chamber, wherein the reaction chamber having an anode rail assembly, a cathode rail, and a gap located between the anode rail assembly and the cathode rail; supplying energy to the anode rail assembly to generate a plasma field in the gap between the anode rail assembly and the cathode rail; and causing the air to flow through the plasma field created in the reaction chamber. The gap between the anode rail assembly and the cathode rail has a central longitudinal axis and further separates the cathode rail from the plurality of discharge anode elements such that the discharge anode elements do not cross the central longitudinal axis of the gap. The anode rail assembly includes an anode rail made of a first conductive material and having a longitudinal axis, and a plurality of discharge anode elements. Each of the plurality of discharge anode elements has a proximal end and a distal end, and the proximal ends may be fixed to the anode rail, and each of the plurality of discharge anode elements may be electrically coupled to each other and to the anode rail. The method may be performed using discharge anode elements having a distal end in the form of a pointed tip, and optionally, the distal ends of the discharge anode elements have a rough surface to assist with discharging electrical current. The cathode rail is made of a second conductive material, is substantially parallel and opposite to the anode rail. The method may generate a plasma field using power characterized by greater than about 1,000 VAC at a frequency of about 60 Hz. Alternatively, the method may generate a plasma field using greater than about 1,000 VAC at a frequency of greater than about 1,000 Hz. Alternatively, the method may generate a plasma field using greater than about 2,000 VAC at a frequency of greater than about 10,000 Hz. The method may be used to create a fan-shaped non-thermal plasma field that emanates from one or more of the plurality of discharge anode elements towards the cathode rail. Preferably, the energy is used to create a plasma field that is substantially homogenous throughout the gap.

An ambient air treatment device capable of operating in at least two modes is also disclosed. The ambient air treatment device includes a reaction chamber having: a first anode assembly and a first cathode rail, wherein the first anode assembly has a first elongate anode rail and a first plurality of discharge anode elements extending outward from the first elongate anode rail; a second anode assembly and a second cathode rail, wherein the second anode assembly has a second elongate anode rail and a second plurality of discharge anode elements extending outward from the second elongate anode rail; an airflow input on a first side of the first anode assembly, the first cathode rail, the second anode assembly, and the second cathode rail; and an airflow output on a second side of the first anode assembly, the first cathode rail, the second anode assembly, and the second cathode rail. In addition to the reaction chamber, the ambient air treatment device includes: a first power supply electrically coupled to the first anode assembly and to the first cathode rail capable of generating a first plasma field between the first anode assembly and the first cathode rail; a second power supply electrically coupled to the second anode assembly and to the second cathode rail capable of generating a second plasma field between the second anode assembly and the second cathode rail; and a control switch. The control switch is configured to permit the ambient air treatment device to operate in at least two modes, including a first mode that uses the first power supply to generate a first plasma field and a second mode that uses the second power supply to generate a second plasma field. Each of the first cathode rail and the second cathode rail may include one or more conductive elements placed in electrical contact with each other so as to form an electrically-conductive, elongated cathode having an upper face, wherein at least a portion of the upper face contains a textured surface for assisting in the generation of plasma. The first anode assembly and said first cathode rail are positioned in spaced relationship opposite each other, and the second anode assembly and said second cathode rail are positioned in spaced relationship opposite each other. Each of the first plurality of discharge anode elements for each of the first anode assembly and the second anode assembly may include a textured surface on a distal end for assisting in the generation of plasma. The first and second power supplies preferably differ in both the magnitude and frequency of the power source being used to generate plasma. For example, the ambient air treatment device may have a first power supply that operates using greater than about 1,000 VAC at a frequency of about 60 Hz, and may have a second power supply may use greater than about 1,000 VAC at a frequency of greater than about 1,000 Hz. Of course, the second power supply may use other power characteristics as well, including for example a second power supply that operates using greater than about 2,000 VAC at a frequency of greater than about 10,000 Hz. Each of the first and second anode assemblies and each of the first and second cathodes rail may be made out of a conductive material comprising at least one of silver, copper, gold, aluminum, zinc, brass, and steel. For example, each of the first and second anode assemblies may be made using a first conductive material selected from: silver, copper, gold, aluminum, zinc, brass, steel, and stainless steel, and each of the first and second cathode rails may be made using a second conductive material, different from the first conductive material, selected from: silver, copper, gold, aluminum, zinc, brass, steel, and stainless steel. The first anode assembly may optionally be elongated having a distance of D1, and the first cathode rail may be elongated, substantially flat and have a distance of less than D1. The second anode assembly may optionally be elongated having a distance of D2, and the second cathode rail may be elongated, substantially flat and have a distance of less than D2. The first plurality of discharge anode elements may extend toward the first cathode rail, and yet remain spaced from the first cathode rail to permit the creation of a first plasma field there between. Similarly, the second plurality of discharge anode elements may extend toward the second cathode rail and yet remain spaced from the second cathode rail to permit the creation of a second plasma field there between. The ambient air treatment device may, further comprising a blower to generate an airflow across at least the first plasma field during operation of the ambient air treatment device. The blower can be used to generate an airflow across the first and second plasma fields during operation of the ambient air treatment device. The blower may optionally have at least two speeds, whereby the air treatment device can operate the blower at a lower speed when generating plasma in the first mode of operation, or can operate the blower at a higher speed when generating plasma in the second mode of operation. The textured surface on the distal end of each of the plurality of discharge anodes may each be formed using a variety of formations to facilitate formation of plasma, including for example, one or more of: a cross-hatch pattern, grooves, etchings, ridges, dimplings, and pittings. Similarly, the textured surfaces on the upper surface of the cathode rails may be formed using a variety of formations to facilitate formation of plasma, including for example, one or more of: a cross-hatch pattern, grooves, etchings, ridges, dimplings, and pittings. The first anode assembly and second anode assembly may be aligned along a common axis and spaced sufficiently to provide electrical isolation from each other during operation. Similarly, the first cathode rail and the second cathode rail may be aligned along a common axis and spaced sufficiently to provide electrical isolation from each other during operation. The control switch can be configured to permit the ambient air treatment device to operate in a first mode using the first power supply to generate a first reactive oxygen species having a first set of characteristics and to permit the ambient air treatment device to operate in a second mode using the second power supply to generate a second reactive oxygen species having a second set of characteristics, different from the first set of characteristics. For example, the first mode may generate a first volume of ROS which have longer-half lives when compared to the second mode which may generate a smaller volume of ROS with longer half-lives. The ambient air treatment device may utilize power supplies that vary in terms of voltage magnitude and frequency. For example, the ambient air treatment device may use a first power supply that generates plasma using greater than about 5,000 VAC at a frequency of about 60 Hz, and the second power supply may generate plasma using greater than about 5,000 VAC at a frequency of greater than about 10,000 Hz. Alternatively, the ambient air treatment device may use a first power supply that generates plasma using greater than about 2,000 VAC at a frequency of about 60 Hz, and wherein the second power generates plasma using greater than about 1,000 VAC and a frequency of greater than about 1,000 Hz. Optionally, the control switch can be configured to permit the ambient air treatment device to operate in at least a third mode that uses the first power supply to generate a first plasma field while simultaneously using the second power supply to generate a second plasma field.

Also disclosed is an air treatment apparatus comprising: an intake portion and an output portion; a reaction chamber located between the intake portion and output portion, wherein the reaction chamber includes an anode rail assembly and a cathode rail assembly; an intake blower located in the intake portion, wherein the intake blower is configured to draw air into the reaction chamber; and power supply circuitry capable of delivering sufficient energy to generate a plasma field in the space between the anode rail assembly and the cathode rail assembly. The anode rail assembly includes an anode rail made of a conductive material and having a longitudinal axis; and a plurality of discharge anode elements, each of which elements has a proximal end and a distal end, with the proximal ends of the discharge anode elements being fixed to the anode rail, and with each of the discharge anode elements being electrically coupled to each other and to the anode rail. The cathode rail assembly includes a cathode rail made of a conductive material and having a longitudinal axis; and a plurality of cathode elements, each of which elements has a proximal end and a distal end, with the proximal ends of the cathode elements being attached to the cathode rail, and with each of the plurality of cathode elements being electrically coupled to each other and to the cathode rail. Preferably, the cathode rail is substantially parallel to the anode rail, and the anode rail assembly and the cathode rail assembly are spaced relative to each other so as to form a space between them, such that the space has a central longitudinal axis and further separates the plurality of cathode elements from the plurality of discharge anode elements such that the discharge anode elements are on one side and do not cross the central longitudinal axis of the space and the plurality of cathode elements are on the opposite side of and do not cross the central longitudinal axis of the space. The air treatment apparatus may optionally include a sensor to monitor triatomic oxygen. Preferably, the sensor is located externally to the apparatus and wirelessly communicates with the air treatment apparatus. While the anode rail assembly and the cathode rail assembly may be made of the same conductive material, they can also be formed using different conductive materials. For example, the anode rail assembly and the cathode rail assembly may be made of conductive materials selected from the group consisting of silver, copper, gold, aluminum, zinc, brass, steel and alloys of the foregoing elements. Optionally, at least a portion of an outer surface of the distal ends of each of the plurality of discharge anode elements and of each of the plurality of cathode elements is textured to facilitate formation of plasma. Optionally, the plurality of cathode elements may be spaced such that each of the cathode elements is equally distant from the two closest discharge anode elements to facilitate the generation of a plasma field in the space between the anode rail assembly and the cathode rail assembly. The power supply may generate plasma using a variety of voltage levels and frequencies. For example, the power supply circuitry may generate plasma using greater than about 1,000 VAC at a frequency of about 60 Hz. Alternatively, the power supply circuitry may generate plasma using greater than about 1,000 VAC at a frequency of greater than about 1,000 Hz. Alternatively, the power supply circuitry may generate plasma using greater than about 2,000 VAC at a frequency of greater than about 10,000 Hz.

Also disclosed herein is a method of generating a plasma field comprising the steps of: drawing air into a reaction chamber having an anode rail assembly, a cathode rail assembly and a gap there between; supplying energy to at least the anode rail assembly to generate a plasma field in the gap between the anode rail assembly and the cathode rail assembly; and causing the air to flow through the plasma field created in the reaction chamber. The anode rail assembly includes: an anode rail made of a conductive material and having a longitudinal axis; and a plurality of discharge anode elements; wherein each of the plurality of discharge anode elements has a proximal end and a distal end, the proximal ends of the discharge anode elements are fixed to the anode rail, and each of the plurality of discharge anode elements are electrically coupled to each other and to the anode rail. The cathode rail assembly includes: a cathode rail made of a conductive material and having a longitudinal axis; and a plurality of cathode elements extending from the cathode rail; wherein each of the plurality of cathode elements has a proximal end and a distal end, the proximal ends of the cathode elements are attached to the cathode rail, and each of the plurality of cathode elements are electrically coupled to each other and to the cathode rail. The cathode rail may be substantially parallel to the anode rail; and the anode rail assembly and the cathode rail assembly may be spaced relative to each other so as to form a gap between them. The gap has a central longitudinal axis and further separates the plurality of cathode elements from the plurality of discharge anode elements such that the discharge anode elements are on one side and do not cross the central longitudinal axis of the gap and the plurality of cathode elements are on the other side and do not cross the central longitudinal axis of the gap. The distal ends of each of the discharge anode elements and of each of the cathode elements may comprise a pointed tip, and optionally, the distal ends of each of the discharge anode elements and of each of the cathode elements have a rough surface to assist with discharging electrical current. The step of supplying energy may be met by supplying energy using greater than about 1,000 VAC at a frequency of about 60 Hz. Alternatively, the step of supplying energy may be supplying energy using greater than about 1,000 VAC at a frequency of greater than about 1,000 Hz. Alternatively, the step of supplying energy may be supplying energy using greater than about 5,000 VAC at a frequency of greater than about 10,000 Hz.

Yet another method of generating non-thermal plasma is disclosed, which includes the steps of: using a first power supply to create plasma in a first plasma field in a reaction chamber wherein the plasma created by the first power supply includes a first volume of reactive oxygen species having a half-life of less than about 10 seconds and includes no more than a second volume of a reactive oxygen species having a half-life of greater than about 1 minute; using a second power supply to create plasma in a second plasma field in the reaction chamber wherein the plasma created by the second power supply includes less than the first volume of reactive oxygen species having a half-life of less than about 10 seconds and includes more than the second volume of a reactive oxygen species having a half-life of greater than about 1 minute. The method may include operating the first power supply to generate plasma while the second power supply is not being used to generate plasma. Alternatively, the method may include operating the second power supply to generate plasma while the first power supply is not being used to generate plasma. Alternatively, the method may include operating the first power supply to generate plasma while simultaneously operating the second power supply to generate plasma. The method may include using the first power supply to generate plasma using energy at greater than about 1,000 VAC at a frequency of about 60 Hz. Alternatively, the method may include using the second power supply to generate plasma using energy at a voltage of about 1,000 VAC or greater and at a frequency of about 1,000 Hz or greater.

Yet another device for generating non-thermal plasma is disclosed, which device has at least two modes of operation. The multi-mode device includes a reaction chamber having: a first reactor and a first power supply to create plasma in a first plasma field, wherein the plasma created by the first power supply includes a first volume of reactive oxygen species having a half-life of less than about 10 seconds and includes no more than a second volume of a reactive oxygen species having a half-life of greater than about 1 minute; and a second reactor and a second power supply to create plasma in a second plasma field, wherein the plasma created by the second power supply includes less than the first volume of reactive oxygen species having a half-life of less than about 10 seconds and includes more than the second volume of a reactive oxygen species having a half-life of greater than about 1 minute. Power supplies having at least one of different voltage magnitudes and frequencies are used. For example, the first power supply can generates plasma using energy at greater than about 1,000 VAC at a frequency of about 60 Hz, and the second power supply can generate plasma using energy having a voltage of about or greater than 1,000 VAC and a frequency of about or greater than 1,000 Hz. Alternatively, the second power supply can generate plasma using energy having a voltage of about or greater than 10,000 VAC and a frequency of about or greater than 10,000 Hz.

DETAILED DESCRIPTION OF THE INVENTION

The present invention provides an apparatus for generating a non-thermal plasma field for generating ROS. The present invention relates to apparatuses and methods for treating air to help neutralize airborne contaminants such as micro-organisms, viruses, and bacteria. The air treatment apparatuses disclosed herein are capable of constantly producing non-thermal plasma discharge by means of a physical array having at least one anode and cathode (at least one of which includes a plurality of extensions) and power supplies that deliver sufficient energy to create a non-thermal plasma field between the anode and cathode. A "corona" is a process by which a current develops from an electrode with a high potential in a neutral fluid, usually air, by ionizing that fluid to create plasma around the electrode. The ions generated pass charge to nearby areas of lower potential, or recombine to form neutral gas molecules. When the potential gradient is large enough at a point in the fluid, the fluid at that point ionizes and it becomes conductive. Air near the electrode can become ionized (partially conductive), while regions more distant do not. When the air becomes conductive, it has the effect of increasing the apparent size of the conductor region. Since the new conductive region is less sharp, the ionization will not extend past this local region. Outside of this region of ionization and conductivity, the charged particles slowly find their way to an oppositely charged object and are neutralized. The non-thermal plasma produced contains ROS that have a much higher reactivity than oxygen in the form of stable oxygen molecules. The ROS produced include atomic oxygen, singlet oxygen, hydrogen peroxide, superoxide anion, tri-atomic oxygen and hydroxyl radicals. The ROS attach themselves to the surfaces of pathogen at bond sites to create strong oxidizing radicals. These radicals draw out the hydrogen that is present in these contaminants breaking down the surface membranes and rendering them inactive. Species within the group of ROS have different half-lives. For example, it is known that hydrogen peroxide has a half-life of less than a second. This is in contrast to tri-atomic oxygen, i.e., ozone, for which studies and testing show that it can sustain a half-life up to 20 minutes, depending on the bio load within the treated area.

Figure 1:
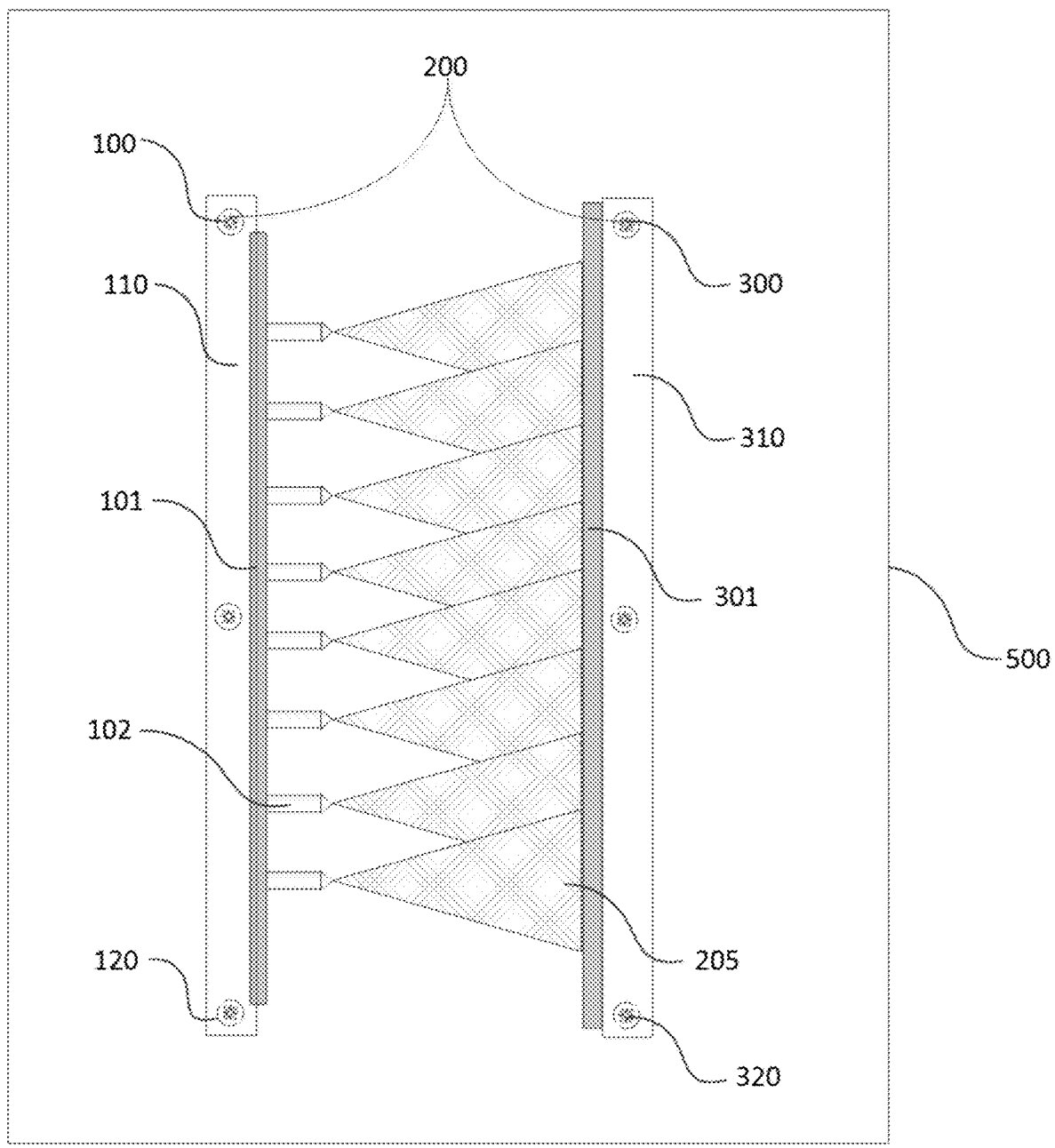
FIG. 1 depicts the interior of the reaction chamber including the anode rail assembly and the cathode rail which make up the reactor.

FIG. 1 depicts the interior of an exemplary reaction chamber 500 (including the anode rail assembly 100 and the cathode rail assembly 300 which make up a reactor 200. The anode rail assembly 100 includes an anode rail 101, anode discharge elements 102, and an anode rail support 110. The cathode rail assembly 300 includes a cathode rail support 310 and a cathode rail 301. As illustrated in FIG. 1, the anode rail assembly 100 and the cathode rail assembly 300 are separated by an air gap (or space where a plasma field 205 can be generated). When sufficient power is supplied to the reactor 200, fan-shaped non-thermal plasma fields 205 are generated which generate ROS when ambient air is passed through the plasma field.

In some embodiments, the reaction chamber 500 may contain a plurality of reactors 200. For example, there may be at least 2, 3, 4, 5, or 6 reactors 200 within a single reaction chamber 500, and each reactor may have a separate power supply. In one embodiment, for example, at least one reactor 200 is connected to a low voltage power supply at line frequency (60 Hz) and at least one other reactor 200 is connected to a high voltage power supply at a much higher frequency. In yet another embodiment, two or more of the plurality of reactors 200 are each connected to its own respective high voltage power supply to permit each individual reactor to be powered on or off individually. In this latter embodiment, the volume of production of ROS having longer half-lives can be varied simply by turning on or off additional reactors. By way of further example, if two reactors are both being operated using high voltage power supplies, one can reduce the volume of longer-half-life ROS (e.g., ozone) by half simply by turning off one of the two reactors.

Figure 2:
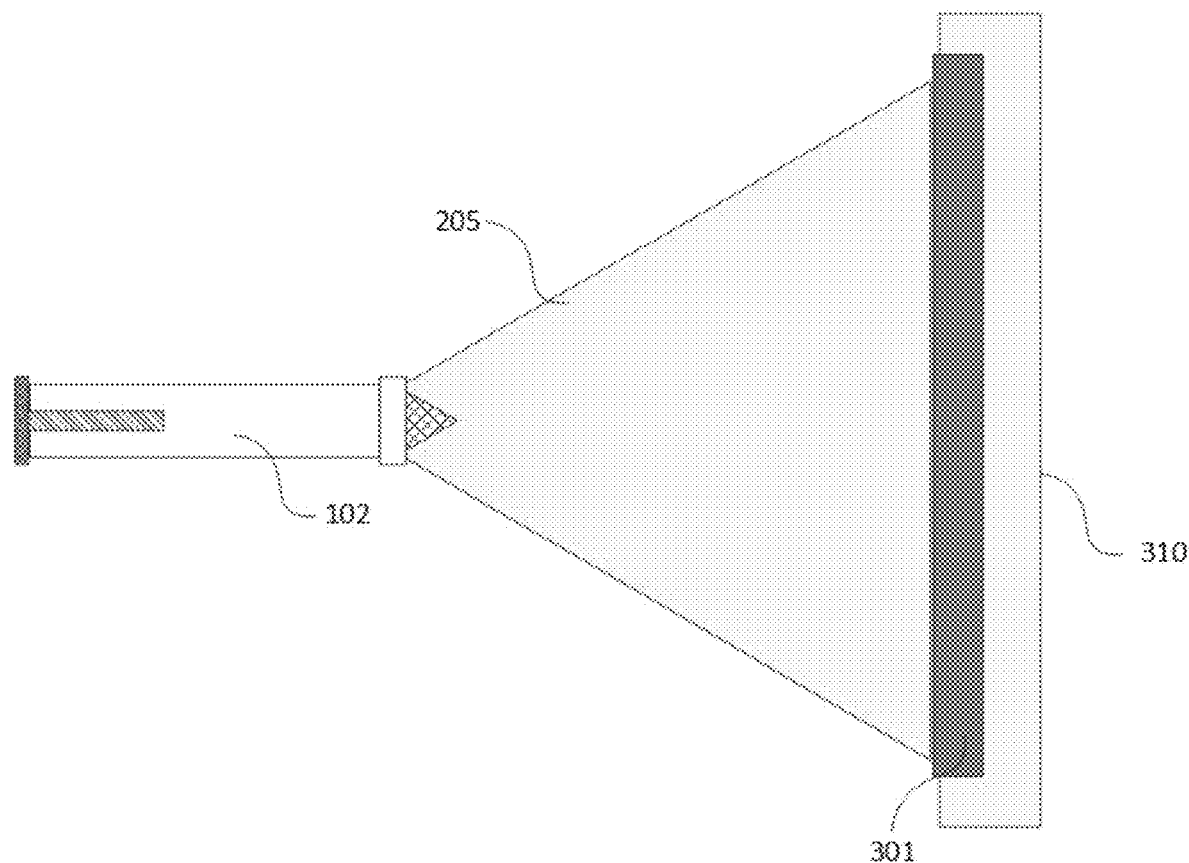
FIG. 2 generally depicts a fan-shaped non-thermal plasma field that can be generated using a single anode discharge element consistent with the reaction chamber of FIG. 1.

FIG. 2 generally depicts a fan-shaped non-thermal plasma field 205 that can be generated using a single, isolated anode discharge element 102 consistent with the reaction chamber of FIG. 1.

Figure 3:
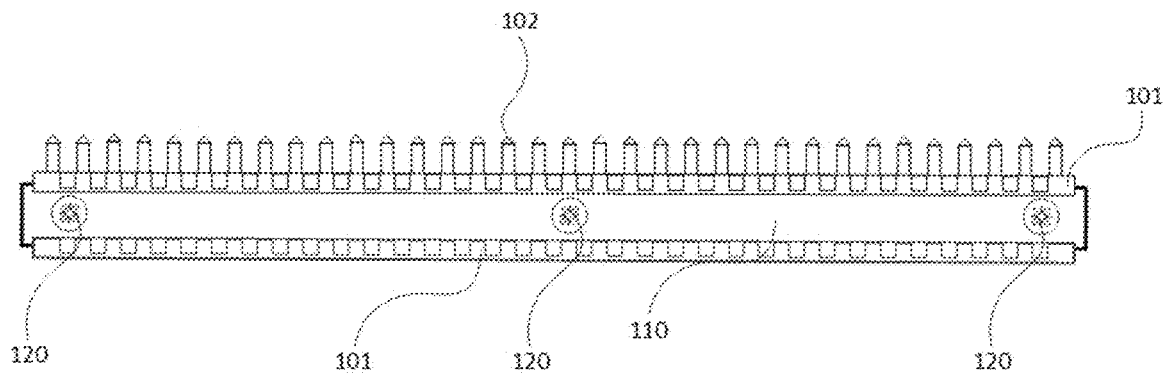
FIG. 3 illustrates the details of the anode rail assembly of FIG. 1

FIG. 3 illustrates the details of the anode rail assembly 100 of FIG. 1. The anode rail assembly 100 includes an anode rail 101 made of a first conductive material and has a longitudinal axis (not shown). The anode rail 101 has a plurality of discharge anode elements 102. Each of the discharge anode elements 102 has a proximal end and a distal end. The proximal ends of the discharge anode elements 102 can be permanently or removable fixed to the anode rail 101. The anode rail assembly may be secured using connection studs 602 and nylon screw (not depicted) that affix the anode rail 101 to the anode rail support 110 via the mounting point 120. The anode rail support 110 is made of non-conductive material to isolate the anode rail from the other components of the reaction chamber. The connection studs 602 are preferably nylon in order to eliminate any cross connections.

Figure 4:
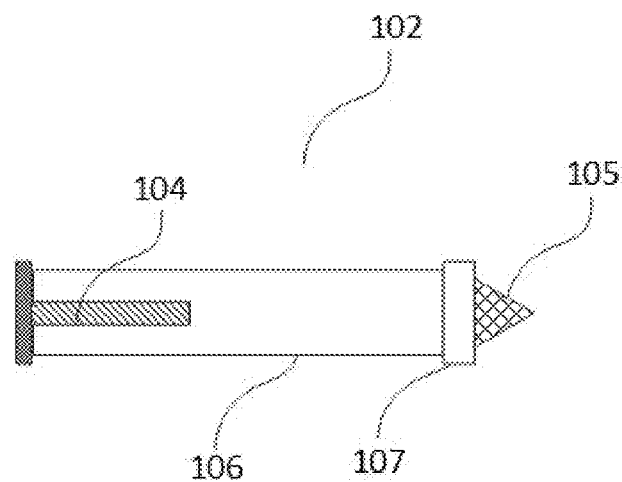
FIG. 4 is a close up drawing illustrating the details of one of the plurality of discharge anode elements of the anode rail assembly of FIG. 1.

FIG. 4 is a close up drawing illustrating the details of one of the plurality of discharge anode elements 102 of the anode rail assembly of FIG. 1. The anode discharge element 102 has internal threads 104 located on one end to permit a conductive bolt to be connected the anode discharge element 102 to the anode rail 101. While the discharge anode element 102 can be formed as a unitary piece, it can also be milled as multiple parts and then assembled. For example, the tip 105 may be formed as part of, or be formed separately and then secured to, the anode discharge element 102. Tip 105 may be rounded or conical (as illustrated), and preferably, has a textured surface, such as a rough milled surface, for better conductivity. Another part of the discharge anode element 102 may be an isolation cup 107 to help control the gradient potential. The textured surface of the tip 105 can also comprise one or more of grooves, cross-hatching, etchings, ridges, dimplings, and pittings.

Figure 5:
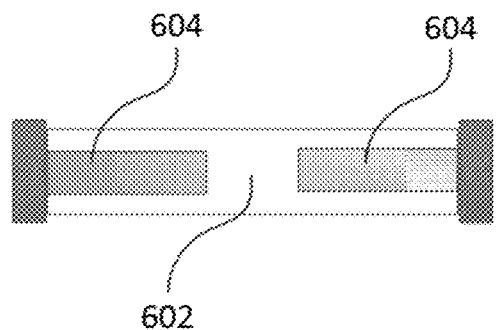
FIG. 5 is a close up drawing illustrating the details of a connection stud for securing an anode rail or cathode rail to the reaction chamber.

FIG. 5 is an illustration of a connection stud 602. Both the anode rail and cathode rail may utilize at least one connection stud 602, and preferably, multiple connection studs 602. The connection stud 602 may have two sets of internal threads 604 located at each end of the connection stud 602. This connection stud 602 is mounted to the conductive rails (e.g. anode rail 101 and cathode rail 301) at the mounting points 120, 320 on the rails (see, e.g., FIG. 1). The rails are then secured through each support rail 210, 310 using non-conductive screws (not depicted) which mate with the threads in the connection studs 602. Preferably, the screws and connection studs are made of nylon. The use of the nylon serves two requirements. One is that the screws are non-conductive and eliminate the ability to create a cross connection and/or short. The other is that the nylon material has the ability to withstand the ROS being created within the reaction chamber. Testing has shown that tri-atomic oxygen has the ability to break down rubber and some plastics, whereas nylon can withstand the effects of tri-atomic oxygen.

Figure 6:
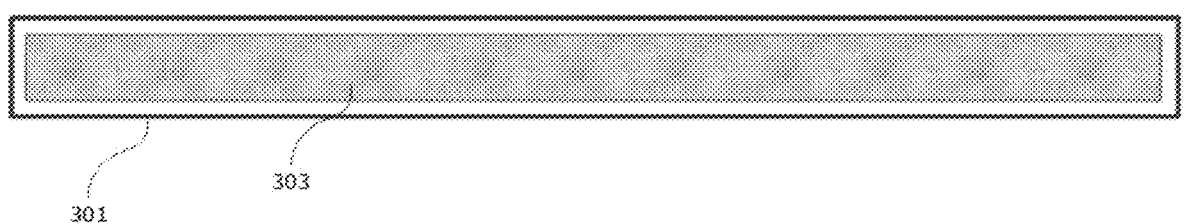
FIG. 6 illustrates the details of the cathode of FIG. 1

FIG. 6 illustrates the details of the cathode of FIG. 1 The cathode rail 301 is elongated and is substantially flat, and may be about 1-3 inches wide and at least twice as long as wide. Preferably, at least a portion of an upper surface of the cathode rail 301 is textured (as described in detail elsewhere in this specification), which is illustrated by textured area 303, which facilitates formation of a plasma field.

Figure 7:
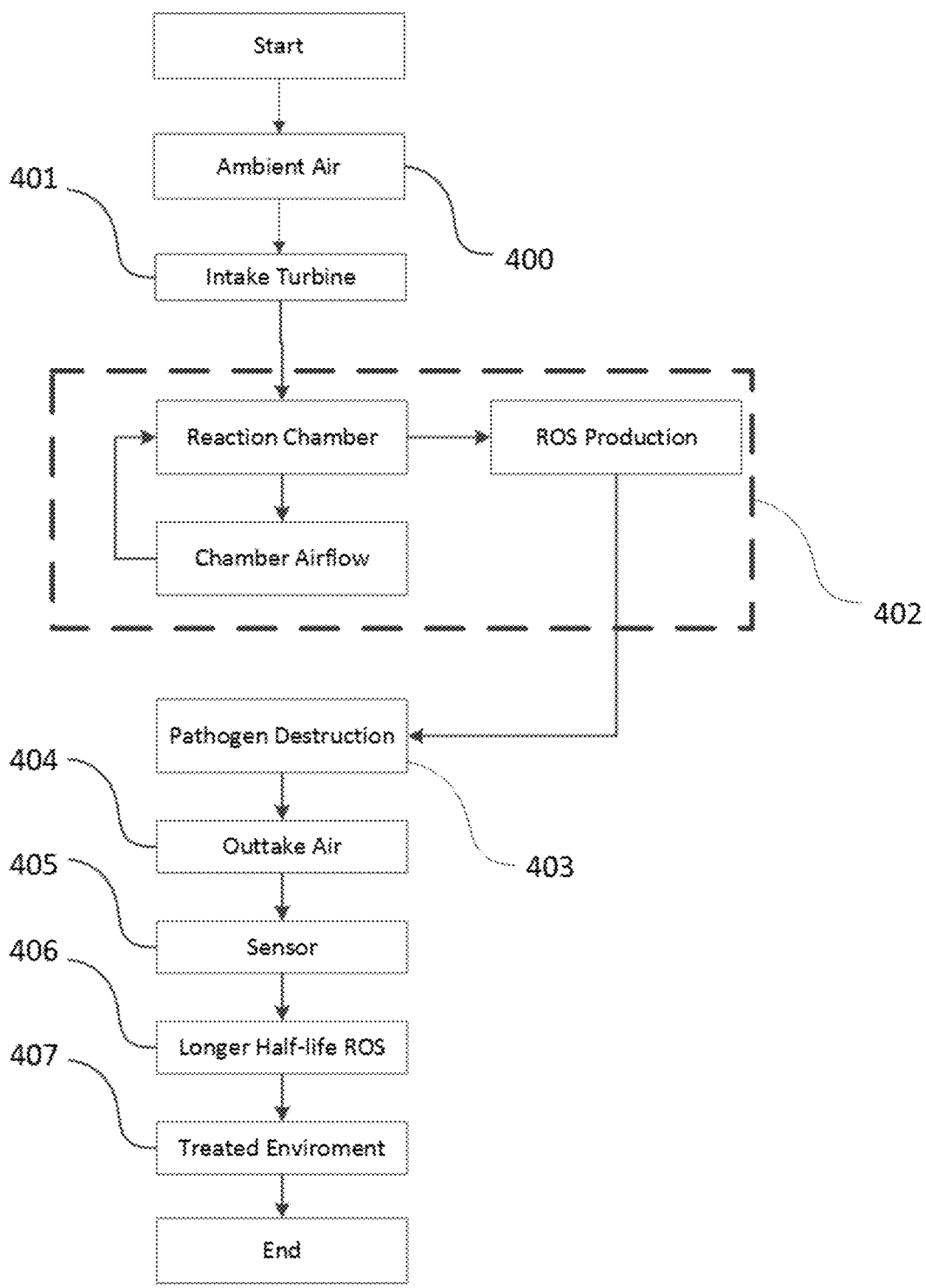
FIG. 7 is a block diagram illustrating different aspects of a process by which air can be treated using a plasma field generated in a reaction chamber.

FIG. 7 is a block diagram illustrating different aspects of a process by which air can be treated using a non-thermal plasma field generated in a reaction chamber. FIG. 7 outlines a process of the present invention where ambient air 400 is drawn into the reaction chamber process 402 with the use of an intake turbine in step 401 (which could utilize a blower in lieu of a turbine). Once in the reaction chamber, the oxygen molecules, through the production of non-thermal plasma, are converted into ROS as part of the reaction chamber process 402. Once created, the ROS attach themselves to the surfaces of pathogens at bond sites to create strong oxidizing radicals. These radicals draw out the hydrogen that is present in these contaminants breaking down the surface membranes and rendering them inactive, as part of pathogen destruction process 403. The treated air and some low residual species, mainly atomic oxygen, singlet oxygen, hydrogen peroxide, superoxide are then released as part of the outtake air process 404 into the treated environment in step 407. The process may optionally include a sensor step 405 to monitor ROS product from the reaction chamber process 402. Optionally, when producing certain ROS which have an extended half-life (e.g., a tri-atomic oxygen species with a half-life of 20 minutes), it may be preferable to use a catalytic filter (such as a manganese dioxide filter as discussed in greater detail below) to neutralize such tri-atomic oxygen species as part of optional step 406 prior to being released in the treated environment in step 407.

Figure 8:
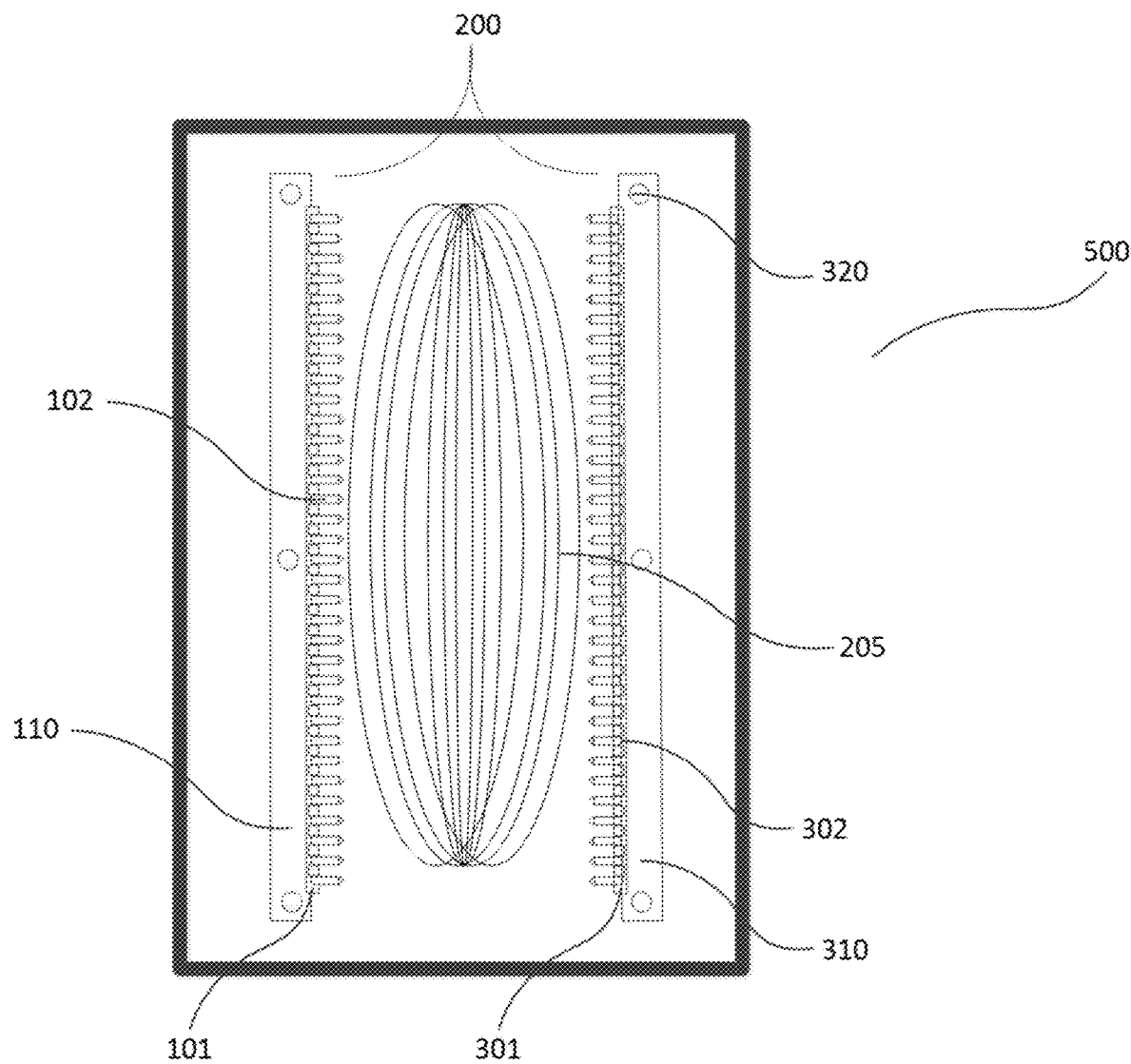
FIG. 8 depicts a reaction chamber having an anode rail assembly and cathode rail assembly positioned such that the plurality of anode discharge elements face a plurality of cathode elements in a cross-point configuration.

Referring now to FIG. 8, the reaction chamber 500 is constructed from a non-metallic chamber that houses a cross point discharge reactor 200. In a preferred embodiment, the chamber is round to promote improved airflow. The reactor 200 has two high voltage rails, one of which is a cathode rail assembly 200 and one that is the anode rail assembly 300. The cathode rail assembly 200 may be connected to a power supply, as described elsewhere herein. The anode rail assembly 100 is connected to the output of the same power supply. The two rails are separated by an air gap where the non-thermal plasma 205 is produced. Each rail is attached the support structure with the use of nylon screws and non-conductive connection studs 602 in order to eliminate cross connections. In the embodiment shown in FIG. 8, each of the anode rail assembly 100 and the cathode rail assembly 300 includes a rail (anode rail 101, cathode rail 301) that has multiple discharge points/receptors (anode discharge elements 102, and cathode elements 302). During operation, a plasma field 205 is generated in the gap between the anode rail assembly 100 and the cathode rail assembly 300. One of skill in the art would appreciate that the gap is determined in part based on the magnitude of the voltage being used to create the plasma field. One of skill in the art would also appreciate that the size of the gap is also impacted by the conductive material of the anode rail 101 and the cathode rail 301. Preferably, the gap is less than a few inches, and more preferable, the gap is less than 1 inch. More preferably, the gap is less than about 0.75 inches. By way of examples, the anode assembly and the cathode rail may be separated by an air gap of approximately four inches (4") when applying a voltage level of 5,000 volts, by an air gap of about two inches (2") when applying a voltage level of 2,000 volts, and by an air gap of less than an inch when applying a voltage level of 1,000 volts. One of skill in the art would understand how to design and/or select a power supply that could be used with the inventions disclosed herein, including for example, using a power supply such as the OZ120WAC Ozone Power Supply by Chirk Industries, which can utilize either 95-125 VAC or 200-250 VAC and can provide power having 3-20 KV and a frequency of 10 KHz to 35 Khz.

In one embodiment the invention is an air treatment apparatus. The air treatment apparatus may have an intake portion and an output portion. The air treatment apparatus may also contain a reaction chamber located between the intake portion and output portion.

The reaction chamber may have an anode rail assembly. The anode rail assembly has an anode rail made of a first conductive material and has a longitudinal axis. The anode rail also has a plurality of discharge anode elements. Each of the plurality of discharge anode elements has a proximal end and a distal end. The proximal ends of the discharge anode elements can be permanently or removably fixed to the anode rail. Each of the plurality of discharge anode elements is electrically coupled to each other and to the anode rail.

In some embodiments, the reaction chamber includes a cathode rail that is made of a second conductive material. The cathode rail can be a solid metal bar or it can comprise a plurality of metal elements electrically coupled to each other such that they collectively serve as a rail. Preferably the plurality of metal elements are spaced adjacently to each other so as to form a substantially continuous rail even though it may comprise multiple elements. The cathode rail is substantially parallel to the anode rail, and preferably uniformly and evenly spaced from the anode rail. The cathode rail is located opposite from and generally faces the plurality of discharge anode elements. In one particular embodiment, the anode rail assembly and the cathode rail are located relative to each other so as to form a space (or gap or void), wherein the space has a central longitudinal axis and further wherein the space separates the cathode rail from the plurality of discharge anode elements such that the discharge anode elements do not cross the central longitudinal axis of the space. The space permits a plasma field to be generated during operation, and preferably, the plasma field is a non-thermal plasma field.

In alternative embodiments, the apparatus includes a cathode rail assembly that comprises a rail and a plurality of cathode elements extending from the rail. Each of the plurality of cathode elements has a proximal end and a distal end. The proximal ends of the cathode elements can be permanently or removably fixed to the cathode rail, and each of the plurality of cathode elements is electrically coupled to each other and to the cathode rail. When the cathode rail assembly is opposite the anode rail assembly, the distal ends of the cathode elements generally face the distal ends of the discharge anode elements. The cathode elements may be placed directly opposite the discharge anode elements; preferably, however, the cathode elements are spaced such that each of the cathode elements is spaced equally distant from the two closest discharge anode elements to facilitate the generation of a plasma field in the space between the anode rail assembly and the cathode rail assembly. The cathode rail has an upper surface, and preferably, at least a portion of the upper surface is textured. In some embodiments, the middle of the upper surface is textured. In some embodiments the cathode rail is at least about 1, 2, or 3 inches wide and is at least about 8, 9, 10, 11, 12, 13, or 14 inches long. In some embodiments the anode rail assembly is at least about 1, 2, or 3 inches wide and is at least about 6, 7, 8, 9, or 10 inches long. Preferably, the anode rail assembly is shorter in length than the cathode rail. Preferably, the textured surface of the cathode rail faces the distal ends of the discharge anode elements. The textured surface of the cathode rail may comprise one or more of grooves, cross-hatching, etchings, ridges, dimplings, and pittings.

The air treatment apparatus of the embodiments discussed above may also have an intake blower located in the intake portion. The intake blower is configured to draw air into the reaction chamber. The blower may be adjustable to control the flow rate of air through the reaction chamber. For example, when using a low voltage power supply and/or when generating ROS with very short half-lives, an airflow rate of 60-70 CFM may be sufficient. When using a high voltage/high frequency power supply (which generates a greater volume of ROS with longer half-lives), a higher air flow rate, for example, 120-200 CFM, may be more desirable to treat air and contaminants outside of the reaction chamber. Such a configuration would be preferred in environments where there is a need to treat surrounding air and surfaces, such as in an unoccupied hospital room in between surgeries. In addition, using different intake blowers may be useful in treating different sized areas. For example, a 120 CFM blower can increase airflow through a reactor which then increases the ability of the reactor to circulate more ROS in any given time. Any number of blower fans on the market could be used, including for example, the Fantech FR100, FR110, FR125, FR140, FR200, and FR250 models. One of skill in the art would select a blower fan based on the environment in which a treatment apparatus is being place or is expected to be used.

In alternative embodiments, however, the air treatment apparatus may be placed in an existing duct or other air flow where by the air is forced to flow through the reaction chamber which will obviate the need for an intake blower being incorporated into the air treatment apparatus.

The air treatment apparatus may include power supply circuitry capable of delivering sufficient energy to generate a non-thermal plasma field in the space between the anode rail assembly and the cathode rail, or between the anode rail assembly and the cathode rail assembly in those alternative embodiments having the cathode rail assembly. The power supply circuitry may comprise a line voltage power supply (using standard household AC (e.g., 60 Hz, 120 VAC to generate a 1,000 VAC at 60 Hz)) to create a non-thermal plasma field having a first set of characteristics (e.g., a production of different ROS that includes a substantial volume of highly reactive species having relatively short half-lives (e.g., less than 1 second)). The voltage may be applied to the anode, and the cathode shares a common ground with the power supply. The power supply may utilize a transformer or other known circuitry to deliver energy at frequencies and voltages higher than those associated with standard household AC in order to create a non-thermal plasma field having ROS with a second set of characteristics, which are different from those generated using standard AC power (e.g., a production of different ROS that includes a substantial volume of less-reactive species having relatively long half-lives (e.g., greater than 1 minute). For example, through testing it has been learned that high voltages, e.g., greater than about 1,000 VAC at a frequency of greater than about 1,000 Hz, produce greater volumes of ROS having longer half-lives than the volumes of such ROS generated using lower voltages and frequencies, e.g., 120 VAC at 60 Hz to generate 1,000-5,000 VAC at about 60 Hz. (For purposes of this application, it should be understood that the references to frequencies greater than line frequency are intended to refer to frequency "under load"—in other words, the frequency as would appear during operation at the anode rail.). In other embodiments the power supply operates using greater than about 2,000 VAC at a frequency of greater than about 10,000 Hz. In yet other embodiments the power supply operates using greater than about 4,000 VAC at a frequency of greater than about 15,000 Hz. In additional embodiments the power supply operates using greater than about 5,000 VAC at a frequency of greater than about 10,000 Hz. The high-frequency power is non-fluctuating. One of skill in the art would understand that a variety of power supplies having different voltage levels and operating frequencies could be used with the present inventions. One of skill in the art would select a power supply based upon the environmental conditions in which the apparatus is being used, or based upon the expected application of the apparatus. For example, where it is desired to neutralize pathogens in air, a lower voltage power supply with a lower frequency may be more desirable because ROS with short half-lives can be effectively used to interact with pathogens in the air. On the other hand, where it is desired to treat a larger space, including by neutralizing pathogens that may be on nearby surfaces, the present invention would generate ROS having longer half-lives, and thus a higher voltage, higher frequency power supply would be preferred.

In some embodiments, the reaction chamber 500 may contains a "split core"—which is characterized by the reaction chamber 500 having a plurality of reactors 200, each of which reactor can be coupled to an independent power supply. Preferably at least one reactor 200 is connected to a low voltage power supply having standard line frequency (around 60 Hz) and at least one reactor 200 is connected to a high voltage power supply having a much higher frequency (e.g., more than ten times, more than 100 times); more preferably the voltage of the high voltage supply(ies) is much greater than the voltage of the low voltage power supply. Preferably, each of the plurality of reactors 200 is electrically isolated from the other reactors 200 to reduce the likelihood of electrical interference between the plasma fields. A surprising and unexpected benefit of the "split core" is that the low voltage power supply generates a greater volume of ROS that are highly reactive, such as singlet oxygen species and hydrogen peroxide, but have relatively short half-lives, while the high voltage power supply generates a greater volume of ROS which are less reactive but which have a longer half-lives (this would include, for example, ROS such as ozone). Thus, depending on the environment to be treated, one could selectively produce greater volumes of reactive species having either short half-lives or long half-lives by using a split-core and selectively operating a low voltage power supply and a high voltage power supply. Moreover, as is evident from this unexpected result and from other discussions herein, by using multiple reactors each having a low voltage power supply, one can selectively produce a greater or lesser volume of highly reactive species having relatively short half-lives by selectively turning on or off each of the low voltage power supplies. Similarly, by using multiple reactors each having a high voltage power supply, one can selectively produce a greater or lesser volume of less reactive species having relatively long half-lives by selectively turning on or off each of the high voltage power supplies.

The split core design permits a first power supply to be applied to the first reactor 200, and a second power supply to be applied to the second reactor 200. In some embodiments the amount of power supplied to each reactor 200 is the same, but with the split core, it is possible for the first and second reactors 200 to have entirely different power supplies. While the reactors 200 are electrically isolated from each other, preferably they are spaced near each other. Preferably, they are spaced in line with each other. For example, the first reactor 200 and the second reactor 200 may be aligned along a common axis.

In some embodiments the air treatment apparatus may include a sensor configured to monitor ROS levels in the area of the air treatment apparatus. Preferably the sensor is located externally to the apparatus. The sensor may have a programmable controllable link to the reaction chamber to control the reaction chamber based on collected data received from and/or concentration levels measured by the sensor, thereby permitting a feedback control loop to optimize performance of the air treatment device. The feedback from the sensor can be used, for example to adjust output levels and on/off control of the reaction chamber. In one embodiment, the sensor may be a heated metal oxide semiconductor (HMOS) sensor for tri-atomic oxygen that works by heating a substrate to a high temperature (around 300° F.). At this temperature, the substrate is very sensitive to tri-atomic oxygen. The sensor detects the level of tri-atomic oxygen by measuring the resistance across the substrate. The data from the sensor is then converted into a parts-per-million measurement (PPM) for tri-atomic oxygen. The programmable controllable link may be a programmable logic controller used to monitor the data from the sensor to control the voltage level supplied to the reaction chamber, or turn on or off, one or more reactors in order to control the volume of tri-atomic oxygen being produced. The sensor and the programmable controllable link may communicate wirelessly, for example, using Bluetooth or a Wi-Fi connection such as the 802.11 standard, and variations thereof. One of skill in the art would also appreciate that other controllers could be used, including for example, a microprocessor programmed to monitor measurements and respond to the measurements by adjusting the power supply and/or switching to a different, power supply. In a "split core" reaction chamber 500 having a plurality of reactors each having a high voltage power supply, the programmable link may turn off one or more high voltage power supplies when ozone levels reach a predetermined threshold in the external environment. Moreover, in certain embodiment which include reaction chambers using low voltage power supplies, it may desirable to continue to power one or more of the low voltage power supplies even after turning off the reactors using high voltage power supplies.

The first conductive material of the cathode may be different from the second conductive material of the anode; preferably, however, the first conductive material is the same as the second conductive material. Preferably, the first and second conductive materials are highly conductive. For example, the first conductive material and second conductive material may each be silver, copper, gold, aluminum, zinc, brass, steel, or stainless steel, as well as alloys of the foregoing materials. The stainless steel may be, for example, 200 Series such as 201 or 202, 300 Series such as 304 or 316, ferritic stainless steel, martensitic stainless steel, superaustentic stainless steel, or duplex stainless steel. In addition, the discharge anode elements may be made of a conductive material that is different from the conductive material of the anode rail.

In variations of the embodiments discussed above, at least a portion of an outer surface of the distal ends of the discharge anode elements is textured to facilitate the discharge of electrical energy, thereby enhancing the generation of non-thermal plasma. The textured surface of the distal ends of the discharge anode elements may have one or more of grooves, cross-hatching, etchings, ridges, dimplings, and pittings. The distal ends of the discharge anode elements may also be shaped to form a tip, such as a rounded dome or a conical tip (as illustrated in FIG. 2).

The air treatment apparatus may also have one or more filters. For example, the apparatus may include a manganese dioxide honeycomb filter located on the discharge side of the device. In this embodiment, the filter acts as a catalyst in order to neutralize tri-atomic oxygen in the discharged air when needed. Optionally, an additional filter may be located on the intake side of the device, including, for example, a 30 PPI filter. When placed on the intake side, the filter keeps dust out of the reaction chamber. Optionally, other catalytic filters known to those skilled in the art could be utilized on the discharge side, which could be used in lieu of an exhaust filter.

The anode rails functions as a common electrical bus that is electrically coupled to a plurality of discharge anode elements extending outward from the anode rail.

In some embodiments, the anode assembly is elongated and has a distance of D. The cathode assembly is also elongated, is substantially flat and has a distance of less than D. The plurality of discharge anode elements extend towards the cathode assembly but remain spaced from the cathode assembly to permit the creation of a non-thermal plasma field.

The various embodiments of the apparatus above may be used to perform methods of generating ROS and non-drifting non-thermal plasma fields. The methods comprise drawing air into a reaction chamber of any of the embodiments described above, supplying energy to the anode rail assembly and the cathodes (whether cathode rails or cathode rail assemblies) to generate a non-thermal plasma field in the space between such anodes and cathodes, and causing the air to flow through the plasma field created in the reaction chamber.

The non-thermal plasma field created using such methods may be created using about 120 VAC at a frequency of about 60 Hz which is transformed to about 1,000-5,000 VAC at a frequency of about 60 Hz. In other embodiments the non-thermal plasma field is created using greater than about 1,000 VAC at a frequency of greater than about 1,000 Hz. In yet other embodiments the non-thermal plasma field is created using greater than about 2,000 VAC at a frequency of greater than about 10,000 Hz. In yet other embodiments the non-thermal plasma field is created using greater than about 4,000 VAC at a frequency of greater than about 15,000 Hz. Preferably, energy of a magnitude and frequency is used to create a non-thermal plasma field that is preferably substantially homogenous throughout the gap. The energy may be used to generate a fan-shaped non-thermal plasma field that emanates from one or more of the plurality of discharge anode elements towards the cathode rail.

The ROS created would include but not be limited to atomic oxygen, singlet oxygen, hydrogen peroxide, superoxide anion, tri-atomic oxygen and hydroxyl radicals.

The embodiments described herein can also optionally include a catalytic filter to reduce and or neutralize unwanted Tri-Atomic Oxygen (for example, through the use of a honeycomb manganese dioxide filter). In such a filter, manganese dioxide or other similar reactive material may be heated to a high temperature (e.g., 400° F.) which serves as a catalyst to break down ozone. Such a filter may be desirable for use, for example, in environments where ozone is generally undesirable (e.g., in a hospital room during a patient's operation). If desirable, the reaction chamber could be configured to permit treated air to bypass such a filter altogether, and alternatively to exit through the honeycomb filter for reduction of certain ROS. Such a configuration could be achieved using airflow controls, for example, by using a controllable manifold (e.g., 1:2 manifold that can direct airflow through the honeycomb filter or by-pass it the filter) or by using an adjustable Y-valve.

The foregoing and other aspects, features, details, utilities, and advantages of the present invention will be apparent from reading the following description and claims, and from reviewing the accompanying drawings. Those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An air treatment apparatus comprising:
an intake portion and an output portion;
a reaction chamber located between the intake portion and output portion,
wherein the reaction chamber comprises:
an anode rail assembly comprising:
an anode rail made of a conductive material and having a longitudinal axis, and
a plurality of discharge anode elements, wherein
each of the plurality of discharge anode elements has a proximal end and a distal end,
the proximal ends of the discharge anode elements are fixed to the anode rail, and
each of the plurality of discharge anode elements are electrically coupled to each other and to the anode rail;
a cathode rail assembly comprising:
a cathode rail made of a conductive material and having a longitudinal axis, and
a plurality of cathode elements extending from the cathode rail, wherein
each of the plurality of cathode elements has a proximal end and a distal end,
the proximal ends of the cathode elements are attached to the cathode rail, and
each of the plurality of cathode elements are electrically coupled to each other and to the cathode rail;
wherein the cathode rail is substantially parallel to the anode rail; and
wherein the anode rail assembly and the cathode rail assembly are spaced relative to each other so as to form a space between them, wherein the space has a central longitudinal axis and further wherein the space separates the plurality of cathode elements from the plurality of discharge anode elements such that the discharge anode elements are on one side and do not cross the central longitudinal axis of the space and the plurality of cathode elements are on the other side and do not cross the central longitudinal axis of the space;
an intake blower located in the intake portion, wherein the intake blower is configured to draw air into the reaction chamber; and
and power supply circuitry capable of delivering sufficient energy to generate a plasma field in the space between the anode rail assembly and the cathode rail assembly.

2. The air treatment apparatus of claim 1, wherein the apparatus further comprises a sensor configured to monitor tri-atomic oxygen, wherein the sensor is located externally to the apparatus and wirelessly communicates with the air treatment apparatus.

3. The air treatment apparatus of claim 1, wherein the anode rail assembly and the cathode rail assembly are made of the same conductive material.

4. The air treatment apparatus of claim 1, wherein the anode rail assembly and the cathode rail assembly are made of conductive material selected from the group consisting of silver, copper, gold, aluminum, zinc, brass, steel and alloys of the foregoing elements.

5. The air treatment apparatus of claim 1, wherein at least a portion of an outer surface of the distal ends of each of the plurality of discharge anode elements and of each of the plurality of cathode elements is textured.

6. The air treatment apparatus of claim 1, wherein the plurality of cathode elements are spaced such that each of the cathode elements is equally distant from the two closest discharge anode elements to facilitate the generation of a plasma field in the space between the anode rail assembly and the cathode rail assembly.

7. The ambient air treatment device of claim 1, wherein the power supply circuitry operates at greater than about 1,000 VAC at a frequency of about 60 Hz.

8. The ambient air treatment device of claim 1, wherein the power supply circuitry operates at greater than about 1,000 VAC at a frequency of greater than about 1,000 Hz.

9. The ambient air treatment device of claim 1, wherein the power supply circuitry operates at greater than about 2,000 VAC at a frequency of greater than about 10,000 Hz.

10. A method of generating a plasma field comprising:

drawing air into a reaction chamber, wherein the reaction chamber comprises:
  an anode rail assembly comprising:
    an anode rail made of a conductive material and having a longitudinal axis, and
    a plurality of discharge anode elements, wherein
      each of the plurality of discharge anode elements has a proximal end and a distal end,
      the proximal ends of the discharge anode elements are fixed to the anode rail, and
      each of the plurality of discharge anode elements are electrically coupled to each other and to the anode rail;
  a cathode rail assembly comprising:
    a cathode rail made of a conductive material and having a longitudinal axis, and
    a plurality of cathode elements extending from the cathode rail, wherein
      each of the plurality of cathode elements has a proximal end and a distal end,
      the proximal ends of the cathode elements are attached to the cathode rail, and
      each of the plurality of cathode elements are electrically coupled to each other and to the cathode rail;
  wherein the cathode rail is substantially parallel to the anode rail; and
  wherein the anode rail assembly and the cathode rail assembly are spaced relative to each other so as to form a gap between them, wherein the gap has a central longitudinal axis and further wherein the gap separates the plurality of cathode elements from the plurality of discharge anode elements such that the discharge anode elements are on one side and do not cross the central longitudinal axis of the gap and the plurality of cathode elements are on the other side and do not cross the central longitudinal axis of the gap;
supplying energy to at least the anode rail assembly to generate a plasma field in the gap between the anode rail assembly and the cathode rail assembly; and
causing the air to flow through the plasma field created in the reaction chamber.

11. The method of claim 10, wherein the distal ends of each of the discharge anode elements and of each of the cathode elements comprise a pointed tip.

12. The method of claim 11, wherein the distal ends of each of the discharge anode elements and of each of the cathode elements have a rough surface to assist with discharging electrical current.

13. The method of claim 10, wherein the step of supplying energy comprises supplying energy using greater than about 1,000 VAC at a frequency of about 60 Hz.

14. The method of claim 10, wherein the step of supplying energy comprises supplying energy using greater than about 1000 VAC at a frequency of greater than about 1000 Hz.

15. The method of claim 10, wherein the step of supplying energy comprises supplying energy using greater than about 5,000 VAC at a frequency of greater than about 10,000 Hz.

* * * * *